United States Patent [19]

Ripka

[11] Patent Number: 4,764,471
[45] Date of Patent: * Aug. 16, 1988

[54] CONTINUOUS BIOREACTOR AND PROCESS

[75] Inventor: Michael S. Ripka, Huntingron, Conn.

[73] Assignee: Nabisco Brands, Inc., Parsippany, N.J.

[*] Notice: The portion of the term of this patent subsequent to Apr. 12, 2000 has been disclaimed.

[21] Appl. No.: 568,084

[22] Filed: Jan. 4, 1984

[51] Int. Cl.$^4$ .................. C12N 1/16; C12N 1/18; C12M 1/12; B01D 13/00

[52] U.S. Cl. ................... 435/255; 435/256; 435/311; 435/313; 435/800; 435/813; 435/818; 210/637; 210/651

[58] Field of Search ............. 435/243, 254, 255, 256, 435/287, 311, 313, 800, 813, 818; 426/60; 210/637, 651

[56] References Cited

U.S. PATENT DOCUMENTS

| | | | |
|---|---|---|---|
| 1,687,561 | 10/1928 | Hoffman et al. | 435/255 |
| 3,911,140 | 10/1975 | Osborne et al. | 435/139 |
| 3,940,492 | 2/1976 | Ehnstrom | 435/256 |
| 4,115,147 | 9/1978 | Shimizu et al. | 210/651 |
| 4,218,538 | 8/1980 | Church | 435/101 |
| 4,379,845 | 4/1983 | Ripka | 426/60 |
| 4,416,993 | 11/1983 | McKeown | 435/243 |
| 4,442,206 | 4/1984 | Michaels et al. | 435/68 |
| 4,544,637 | 10/1985 | Keggins et al. | 435/243 |

FOREIGN PATENT DOCUMENTS

| | | | |
|---|---|---|---|
| 1113630 | 5/1968 | United Kingdom | 210/651 |
| 2059436 | 4/1981 | United Kingdom | 435/240 |

OTHER PUBLICATIONS

Larsen, W. F. et al., "Automatic Membrane-Filtration System for the On-Demand Supply of Large Volumes of Sterile Medium in Continuous Culture"; *Biotechnology & Bioengineering*, vol. 18, 1976; pp. 1433-1443.

Klinman et al., "Dialyzable Serum Components Can Support the Growth of Hybridoma Cell Lines In Vitro"; *J. Immunological Methods*, vol. 42; 1981; pp. 1-9.

*Primary Examiner*—Elizabeth Weimar
*Attorney, Agent, or Firm*—Richard Kornutik

[57] ABSTRACT

An improved bioreactor and process for continuously propagating microorganisms, such as yeast, wherein the culture medium is purified in contact with a spirally-wound ultrafiltration membrane and then passed through the outer surfaces of a tubular membrane material for further purification before contact with microorganisms flowing in the interior of the tubular membrane material.

4 Claims, 1 Drawing Sheet

CONTINUOUS BIOREACTOR AND PROCESS

BACKGROUND OF THE INVENTION

The present invention relates to a process and apparatus for continuously propagating microorganisms in a culture medium. More particularly, the present invention relates to a process for continuously propagating microorganisms whereby a crude or precursor culture medium for the microorganism is continuously treated, as an intimate part of the propagation process and apparatus, to provide a suitable purified culture medium for the microorganism.

Numerous biochemical processes are known wherein a microorganism is propagated in a suitable culture medium therefor, either for the purpose of growing large quantities of the microorganism for some particular ultimate purpose or use, or for recovering products produced by the growing microorganism.

Economics and technical considerations generally favor the utilization of a continuous process for these purposes, but, with few exceptions, commercial microorganism propagation processes are conducted as batch or semi-batch processes. Continuous processing has proven to be difficult and, indeed, undesirable for many microorganism propagation systems owing to the inability, among others, to achieve the degree of control required in such processes. This is particularly true with respect to control over the concentration of gaseous materials necessary, or desirably present, in the propagation process, such as oxygen in aerobic propagation systems and oxygen and/or other gases employed in anaerobic systems either to promote or suppress by-product formation, provide suitable gas tensions, or other like functions. In particular, the nature of many microorganism propagation systems is such that the conditions at which they are conducted generally are not particularly conducive to significant solubility of gases in the nutrient or culture medium. As a consequence, gas (e.g., oxygen) utilization in the propagation system is generally quite poor, and resort to use of substantial (e.g., 100 to 1000 fold) excesses above theoretically required gas quantities is not atypical. The need to employ such large quantities of gaseous materials adds considerably to the difficulty of performing the process in a continuous mode and, of course, adds considerably to the expense of the overall process.

Another significant limitation on the possible use of continuous processing in microorganism propagation systems is the substantially universal requirement that the culture medium be purified to remove therefrom microorganisms or other materials which might contaminate the desired microorganisms or the products sought to be recovered therefrom. The degree of purification needed is generally quite high and may involve a number of heat treatments, filtrations or other means for removing undesired materials from the culture medium. In such circumstances, it is quite difficult to develop a process which, from medium purification through microorganism propagation, is truly continuous.

An excellent example of an industry where, despite obvious economic advantages, adoption of a continuous process has been problematic, is the commercial production of yeast.

Commercial yeast production typically is a batch process which entails propagation in a plurality of stages. Generally, yeast are inoculated into a presterilized nutrient medium usually contained in a shaker flask. In the flask, growth of the yeast is encouraged by various means such as controlling the temperature and shaking the flask to effect aeration. The yeast are removed from this flask and inoculated into another flask containing a larger volume of nutrient medium for continued growth. These initial stages may conveniently be referred to as flask or culture development stages.

From the culture development stages, the yeast may be inoculated into a vessel having an air source and means of agitation. These steps may be repeated once or twice using greater amounts of nutrient medium and larger vessels. Because the amount of air used in these stages is generally restricted, these stages are commonly referred to as slightly aerobic stages. Yeast from these stages are then transferred into larger fermentors where vigorous growth conditions are maintained, including the use of large volumes of air. These stages may be referred to as highly aerobic, or commercial, stages since the yeast from these stages are harvested and processed for bakery or home use, typically in compressed or active dry form.

For propagation in the highly aerobic or commercial stages, it is necessary to prepare large quantities of a yeast culture medium which is substantially free of microorganisms. This has been accomplished in the past by sterilizing the medium, such as final molasses, by heat treatment. To reduce the count of contaminating microorganisms to a level effective to produce yeast suitable for food use, large amounts of energy, as well as means for generating and transferring heat to the process, were required. Typically, the heat was generated in oil or gas-fired boilers and transferred to the process as steam which could be injected live or transferred by means of heat exchangers. Subsequent to heating, the molasses would then require cooling prior to use. Thus, this sterilization step entailed sizable capital and operational costs.

In commonly-assigned U.S. Pat. No. 4,379,845 of Apr. 12, 1983, there is disclosed an improved method which eliminates the need for the above-noted thermal sterilization and offers other improvements as well. That method, in its broad aspects, comprises purifying molasses by passing the molasses through an ultrafiltration device (which can be a spirally-wound membrane) effective to reject solids having molecular weights greater than about 30,000 daltons to produce a first permeate, and then passing the first permeate through at least one additional filtration device (which can be a tubular membrane) having an average pore diameter of from about 0.2 to about 1.2 microns to produce a yeast culture medium. The filtration devices are effective in combination to reduce the microorganism count to a level effective to produce yeast suitable for food use. The yeast culture is then inoculated with yeast in a suitable reaction vessel, and the yeast and the yeast culture medium are then subjected to conditions effective to propagate the yeast.

The method of U.S. Pat. No. 4,379,845 provides a significant advance over the prior art with respect to providing a purified culture medium for yeast propagation. The teachings of U.S. Pat. No. 4,379,845 more readily lend themselves to continuous production of yeast than processes theretofore known in the art, but there exists a need for providing a continuous bioreactor and process which would take greatest advantage of this improved method and solve other problems relating to the degree of control over propagation conditions which can be achieved in a continuous process.

Among the so-called continuous reactors presently known are those of Stich in U.S. Pat. Nos. 2,244,902 and 2,657,174, Ehnstrom in U.S. Pat. No. 3,940,492, and Fukuda et al in U.S. Pat. No. 4,284,724.

In U.S. Pat. No. 2,244,902, Stich discloses a process employing a number of interconnected reactors wherein each has means for establishing a vertically-circulating flow of yeast mash and means for introducing air into the downwardly moving portion of the mash. The yeast is circulated within each reactor for a number of cycles and is then transferred to another chamber. The method is said to improve the efficiency of introduction of air as compared to the known reactors wherein cells toward the upper part of the chamber receive relatively low levels of oxygen.

In U.S. Pat. No. 2,657,174, Stich discloses another method for continuous yeast manufacture. According to this method, a yeast mash is withdrawn from a plurality of locations near the bottom of a fermentation chamber, cooled, enriched with nutrients and reintroduced into the chamber at different locations. Within the chamber, the mash flows downwardly, countercurrent to the flow of air into the chambers. Again, the improvement is said to relate to improved oxygen distribution within the reactor. As with the earlier Stich patent, extremely large reactor volumes and separate sources of purified nutrient are required.

Ehnstrom, in U.S. Pat. No. 3,940,492, discloses a process wherein wort is continuously supplied to a circuit including an elongated closed channel through which microorganisms are fed. After fermentation has taken place in the circuit, the mixture of wort and microorganisms is centrifuged to separate it into fermented wort, a living cell mass and impurities. These three components are separately discharged from the centrifuge. The fermented wort and living cell mass are discharged continuously. The living cell mass includes an excess of living cells formed in the circuit. This excess is discharged from the circuit. As with the procedures of Stich, a separate source of sterilized nutrient is required to supply this complex apparatus.

According to the disclosure of Fukuda et al in U.S. Pat. No. 4,284,724, a broth of yeast cells is continously or intermittently removed from a fermentor. Yeast cells then are separated from the filtrate using a cell separator, or further washed with water. The yeast cells so obtained then are recycled to the fermentor, whereby yeasts are cultivated at a high cell concentration of from 6% to about 20% based on dry weight. It is disclosed that by removing the filtrate from the cultivation system, there is no accumulation of metabolities and salts prohibiting the cultivation of yeasts, and the growth of miscellaneous microorganisms which interfere with yeast cell growth is suppressed. As with the other systems, separate means are required to provide sterile nutrient.

There exists a definite need for apparatus and processes which could be employed in a continous operating mode for the propagation of microorganisms in a culture medium, which affords control of the propagation process to the high degree required and which provides for continous purification of culture medium as an intimate part of the process.

SUMMARY OF THE INVENTION

It is an object of the present invention to provide an improved process and apparatus for continuously propagating microorganisms.

Another object of the present invention is to provide an improved process and apparatus for propagating microorganisms wherein the culture or nutrient medium is continuously purified or sterilized as an intimate part of the propagation process.

A further object of the present invention is to provide a process and apparatus for propagating microorganisms wherein gaseous materials required in the propagation process can be employed in enriched form so as to improve gas utilization in the process and reduce overall gas flow requirements.

Yet another more specific object of the invention is to provide an improved process and apparatus for continuously propagating yeast.

Still another more specific object of the invention is to provide an improved process and apparatus for continuously propagating yeast, wherein molasses is continuously purified to provide a culture medium in a manner which permits its immediate use upon purification to continuously propagate the yeast in a reaction zone, in which the purification means is an intimate part, such that cooling and transfer to a separate reactor are not required.

An additional object of the invention is to provide a process and apparatus for continuously propagating yeast wherein oxygen employed in the process is provided as an enriched gaseous stream containing oxygen in a major volumetric amount, and preferably above about 80 percent, whereby overall gas flow requirements in the process are significantly reduced as compared to conventional processes employing dilute oxygen-containing gas streams.

These and other objects are achieved according to the present invention which provides a continous bioreactor apparatus and process for propagating microorganisms in a culture medium.

According to the invention, a nutrient medium is continuously flowed through the length of a cylindrical, spirally-wound ultrafiltration membrane element. The element has a cylindrical outer surface and a concentric cylindrical inner surface which are separated from each other by concentric layers of the spirally-wound membrane. The cylindrical concentric inner surface defines an interior cylindrical space throughout the length of the element. Flow of nutrient medium into the spirally-wound membrane element (typically near the outer surface thereof) results in a radial flow of at least a portion of the nutrient medium through the membrane layers and into the interior cylindrical space. The membrane is sized so as to exclude solids above a predetermined size or molecular weight and, as a result, the nutrient medium passing into the interior cylindrical space is purified to the extent of removal therefrom of solids above a particular size or molecular weight.

The thus-purified medium in the interior cylindrical space of the spirally-wound membrane is then passed along the outer surface of a tubular membrane sized so as to exclude still further solids of predetermined size or molecular weight from the nutrient medium. Within the hollow cylindrical interior of the tubular membrane, the microorganisms to be propagated are passed and contacted with the nutrient medium which has passed through the outer surface of the tubular membrane.

Propagated microorganism and nutrient medium are continuously removed from the hollow cylindrical interior of the tubular membrane (the "reaction" or "propagation" zone) for separation, re-cycle, etc.

Gaseous materials required in the propagation process can be dissolved or dispersed in the nutrient medium passing along the outer surface of the tubular membrane or can be directly introduced into the microorganism stream flowing through the interior of the tubular membrane. Rigorous control over the concentration of gaseous material in the medium in which the microorganism is propagated is attainable by virtue of the increased solubility of the gaseous material in medium flowing under pressure (permitting the use of highly enriched gas streams) and the small total volume of gas required relative to the flow of nutrient medium. The membrane material through which the nutrient medium passes for contact with the microorganism in the hollow cylindrical interior of the tubular membrane aids in the fine dispersion and/or dissolution of gas in the nutrient medium for those cases where the gas is dispersed in the medium passing along the outer surface of the tubular membrane.

In the apparatus, and preferred process of the invention, the tubular membrane is made to be an intimate part of the spirally-wound membrane element by arranging the tubular membrane within the interior cylindrical space defined by the inner surface of the spirally-wound membrane. In this way, the purified nutrient medium from the spirally-wound membrane immediately comes into contact with the outer surface of the tubular membrane and is further purified in passing therethrough into the hollow cylindrical interior of the tubular membrane for contact with the microorganisms therein.

Where gaseous materials are required for the propagation process, the tubular membrane preferably is arranged such that it is within the interior cylindrical space of the spirally-wound membrane but spaced-apart from the cylindrical inner surface of the spirally-wound membrane. In this way, the outer surface of the tubular membrane and the inner surface of the spirally-wound membrane define an annular chamber in which purified nutrient medium from the spirally-wound membrane resides before further passage and purification through the outer surface of the tubular membrane. Required gaseous materials may be introduced into this annular chamber for dispersion and dissolution in the nutrient medium contained therein. As earlier noted, however, the gaseous materials can also be introduced directly into the microorganism stream passing through the tubular membrane.

The apparatus and process are particularly useful in the propagation of yeast in a continuous process wherein nutrient medium (e.g., molasses) can be purified to a degree such that the microorganism count of the medium can be reduced to less than 10, and typically less than 1, count per 100 grams of nutrient medium before contact with the yeast. Rigorous control of oxygen concentrations in the nutrient medium can be achieved so as to provide sufficient oxygen for yeast propagation without exceeding levels at which aerobic fermentation of the nutrient source per se (i.e., carbohydrate to alcohol), without yeast propagation, occurs.

DETAILED DESCRIPTION OF THE INVENTION

Figure 1:
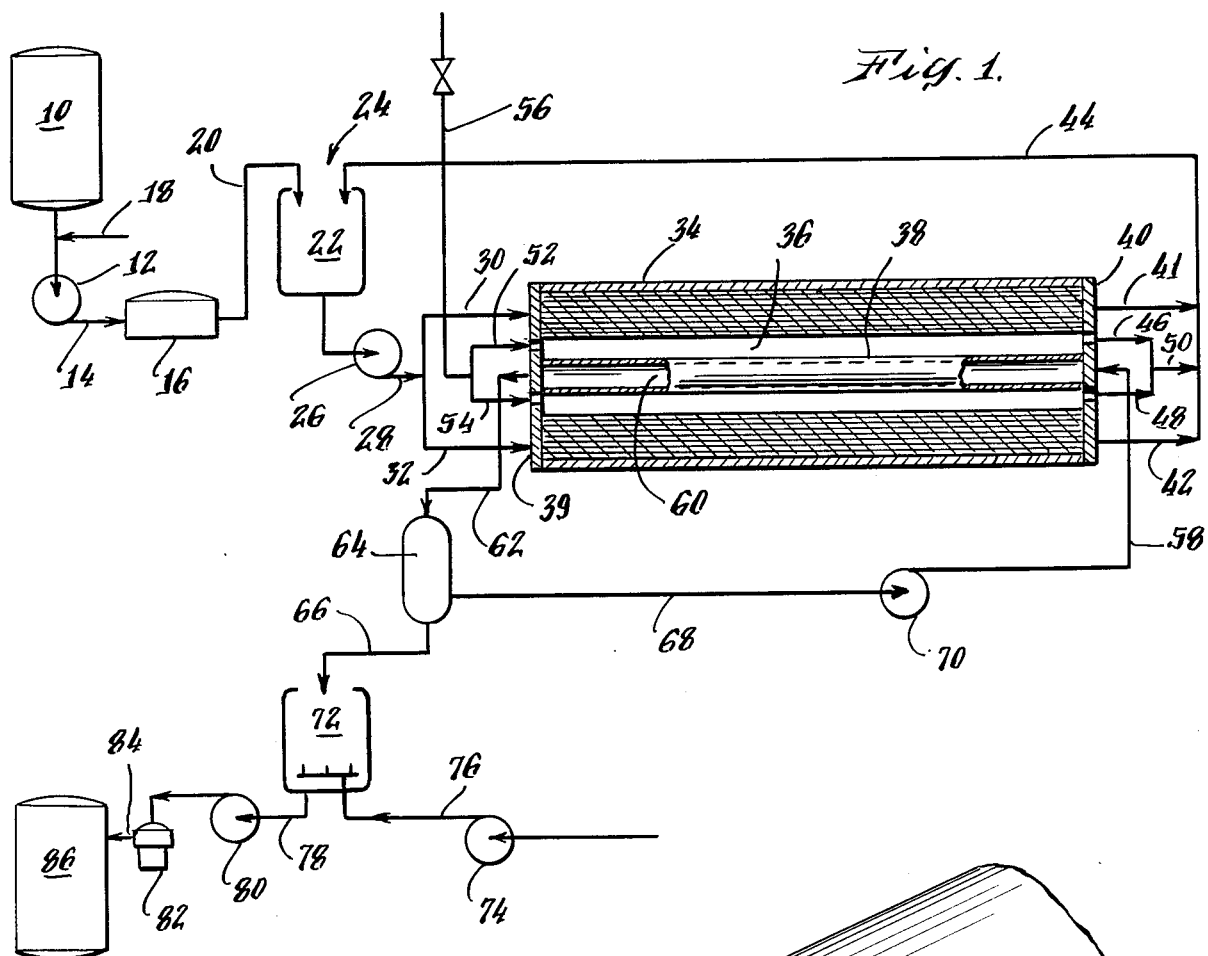
FIG. 1 is a schematic representation of a preferred processing system according to the present invention.

The apparatus and process of the present invention are applicable to a wide variety of microorganism propagation systems wherein microorganisms are grown in contact with a nutrient medium which requires purification or as to which purification is desired. The microorganisms may be those requiring either aerobic or anaerobic conditions for growth.

For purposes of describing details of the apparatus and process, the propagation of yeast in a nutrient medium containing molasses is chosen as illustrative. In this propagation system, the presence of an oxygen-containing gas (e.g., air) is required and, hence, this system will serve to point out a great many features of the invention which are not as readily illustrated with certain other systems.

As applied to the production of yeast, the process of the invention improves the production by continuously purifying a carbohydrate material such as molasses to prepare a culture medium for the yeast in a manner which permits its immediate use upon purification to continuously propagate yeast in a reaction zone comprised in the purification means such that cooling and transfer to a separate reactor are not necessary.

Molasses is the thick liquid which is left after sucrose has been removed from the mother liquor in sugar manufacture from either beets or cane. Molasses does not have an absolutely fixed composition because of the many variations in commercial sugar production and the various stages in the process at which it may be withdrawn. Typically, however, a product known as "final molasses" contains about 20% sucrose, 20% reducing sugars, 10% ash, 20% non-sugar organic materials, and 20% water. This product is essentially the syrup which remains when it is no longer commercially practical to remove further sucrose. This product, also known as "black strap molasses", is typically utilized to produce yeast and various chemicals, such as citric acid and various alcohols, through fermentation.

As the term molasses is used herein, it is meant to include not only final molasses, which has a relatively low economic value due to the high degree of depletion of sucrose, but to other forms of sugar liquors from which significant quantities of sucrose can be crystalized. For example, it is meant to include the mother liquor remaining after the first crystallization of sucrose, commonly referred to as "first molasses". Also included are "second molasses" which is the mother liquor obtained from the second crystallization, as well as each successive stage of molasses on through final molasses. It is also possible to employ whole juice molasses; however, this may not be economically desirable under many conditions.

Likewise, the term molasses is not restricted to molasses produced from any particular source, but can be the end product from a sugar cane or a sugar beet process. In its broad aspects, then, the molasses can be of any sucrose content or botanical source which provides an effective source of carbohydrate for the propagation of yeast.

The yeast culture or nutrient medium may be comprised of the molasses alone or can employ further nutrients, salts and the like as may be necessary to obtain the proper amount of nitrogen, phosphorous, carbohydrate, and minor nutrients as may be required by the particular strain of yeast or its desired end use. It may also be desirable to employ an acid or an alkali to adjust the pH to a suitable value, typically in the range of from about pH 3.5 to about pH 7.

The largest use for viable yeast is for baking purposes, and the process of the present invention is particularly suitable for preparing yeast of this type. Yeast are supplied to bakeries and to consumers for baking in two principal forms, i.e., active dry and compressed. The species of yeast used for baking purposes is generally *Saccharomyces cerevisiae*. There are many strains of yeast which are included within the species and the particular strain used depends upon many factors, such as the desired form of the yeast.

Strains of bakers' yeast can be generally grouped into broad categories when classified according to the bios response procedure published by Shultz and Atkin in ARCHIVES OF BIOCHEMISTRY, Vol. 14, Page 369 (August 1947). The first group is classified as Bios No. 236. Yeast in this group are generally used when it is desired to produce compressed yeast. Compressed yeast are generally formed into bricks of suitable size and contain about 70% moisture. The second group is classified as Bios No. 23, and is typically employed when active dry yeast is to be produced. Although yeast of the Bios No. 23 group can be propagated to higher yields, and are hardier and more stable than yeast of the Bios No. 236 group, compressed yeast of the latter group are preferred by commercial bakers because of their superior leavening activity.

Active dry yeast typically contain less than 10% moisture, and generally from about 4 to 8% moisture. Yeast of the Bios No. 23 group are usually selected for the production of active dry yeast because the properties of yeast of this group, being more hardy and metabolically stable than yeast of Bios No. 236, enables Bios group 23 yeast to be dried to lower moisture levels with minimum loss of initial leavening activity. In some instances, yeast of Bios No. 236 group can be used to prepare an active dry yeast product.

FIG. 1 shows a preferred process scheme for carrying out the present invention. Raw molasses, as stored in tank 10, has a high bacterial count, typically on the order of $10^3$ to $10^7$ microorganisms per gram of liquid molasses, which must be reduced prior to propagation. This is necessary because the conditions for growing the yeast are also highly favorable for the growth of bacteria. It is also necessary to reduce the level of bacteria in all feed streams and process equipment to the lowest practical level. For example, the air supply required for propagating the yeast under aerobic conditions must generally be filtered. Additionally, apparatus must be kept scrupulously clean and be sterilized on a regular basis. Similarly, the yeast itself must be obtained from cultures which are as free as possible from contaminating bacteria.

The raw molasses held in 10 is transferred by means of a positive displacement pump 12, through line 14 to desludger 16. Hot water is added via line 18 and mixed with the raw molasses to give a solution of approximately from about 50° to about 70° brix, and a temperature of from about 120° to about 135° F. The desludger 16 can be either a centrifugal or filter screen unit. The primary purpose of the desludger is to remove particulate matter suspended in the molasses solution, and reject particles greater than about 90–100 microns. One particularly effective desludging unit is a 100 micron SWECO screen system.

Molasses passes from the desludger 16 through line 20 to the feed tank 22. Hot water added via line 24 is mixed with the diluted molasses to give a final concentration of from about 20° to about 50° brix at a temperature of from about 120° to about 130° F. Pump 26 then moves molasses through the ultrafiltration system. The molasses is moved via line 28 to a plurality of radiating lines, shown here as 30 and 32, which feed molasses to a spirally-wound ultrafiltration membrane 34.

The spirally-wound ultrafiltration membrane can be a commercial unit such as an ABCOR Spiral-type membrane cartridge. To be effective for producing products for food use, the ultrafiltration membrane must be capable of rejecting suspended and dissolved solids having molecular weights greater than 30,000 daltons. If desired, ultrafiltration devices which are capable of rejecting solids having molecular weights as low as 10,000 daltons can be employed. Preferably, the device should be capable of rejecting solids having molecular weights above a minimum level of from about 15,000 to about 20,000 daltons.

As the molasses flows through the length of the spirally-wound ultrafiltration membrane 34 in the direction of the longitudinal axis, it is continually under pressure tending to cause all but the higher molecular weight materials to flow radially through the multiple layers of the membrane 34 toward annular chamber 36. Annular chamber 36 is defined by the inner surface of the spirally-wound membrane 34 and the outer surface of a tubular filtration membrane 38. End caps 39 and 40 are the means positioning the tubular membrane within the spirally-wrapped membrane. Thus, the flow of molasses through the spirally-wound membrane 34 establishes a flow of permeate into chamber 36 and towards the second filtration device, tubular filtration membrane 38.

The higher molecular weight materials excluded by the spirally-wound membrane are drawn off via radially positioned ports here shown schematically as 41 and 42 toward recycle line 44 which returns the concentrate portion to feed tank 22. The permeate from the spirally-wound membrane 34 is also caused to flow along the longitudinal axis of the annular chamber 38, with excess being withdrawn via radially spaced lines 46 and 48 and passage into recycle line 44 by line 50.

At the other end of the bioreactor, air or oxygen-enriched gas is introduced via radially spaced lines 52 and 54 from source line 56. Preferably, air dispersing units, such as sintered metal spargers, will be positioned to finely disperse the air within the permeate in annular chamber 36. The flow of the permeate along the extent of the channel 36 will cause air to flow therethrough. Prefereably, the flow of air from entrance lines 52 and 54 to exit lines 46 and 48 will be countercurrent to a flow of a yeast suspension which is passed through the interior of tubular membrane 38 via line 58.

Alternatively, a portion or all the gas can be introduced by a suitable sparging means into chamber 60 (described hereinafter).

The tubular membrane filter will be effective in combination with the spirally-wrapped ultrafiltration membrane 34, to remove substantially all microorganisms from the molasses to produce a yeast culture medium capable of supporting the growth of yeast for food use. The tubular membrane filter will have an average pore diameter of from about 0.2 to about 1.2, preferably from about 0.2 to about 0.5, microns. The permeate passes radially through the tubular membrane cartridge into the reaction zone 60 on the inside of the membrane. Due to the small average pore diameter of the cartridge, air introduced into the permeate in annular chamber 36 is in a finely dispersed and highly dissolved state as it reaches the reaction zone.

A particular advantage of the present invention, as applied to yeast propagation as well as the propagation of other microorganisms where gaseous materials are required, is the ability to achieve rigorous control over the gas concentration in the nutrient medium in which the microorganism is propagated. For example, in yeast systems, highly aerobic conditions are required. Typically, the solubility of oxygen in the nutrient medium is so poor at the conditions at which the propagation is conducted that dilute oxygen streams (e.g., air containing 16 to 20% oxygen) are employed and, further, must be employed in substantial excess over theoretical requirements in order to insure the presence of sufficient dissolved oxygen in the culture medium to effect propagation. In such circumstances, control over oxygen concentrations is difficult to achieve. Moreover, the presence of excess oxygen can cause undesirable results, such as the Pasteur or Crabtree effect (aerobic fermentation of carbohydrates in the medium to alcohol with no yeast propagation).

In the present invention, the pressurized condition of the overall system significantly increases the solubility of oxygen in the nutrient medium. As a result, concentrated oxygen-containing gas streams (for example, prepared by passing air through appropriate oxygen enrichment means, such as molecular sieves) can be employed (containing, e.g., greater than 50%, and typically on the order of 80–95%, oxygen), and the need for utilizing enormous excesses of gas to insure the presence of that required for the propagation is eliminated. In this way, overall gas utilization is improved, equipment requirements for handling large gaseous streams are reduced, and very close control can be maintained as to the volume of oxygen added to the system and the avoidance of excess oxygen.

Another advantage of the process and apparatus of the present invention is a significant reduction in the energy required to operate the system. For example, in conventional batch processes for yeast propagation, overall energy utilization is typically on the order of 550 to 1000 kilowatts per kilogram of yeast (basis, 30% solids). Employing the system of the present invention, energy utilization of 300 kw/kg yeast and lower can be achieved as a result of, e.g., eliminating the need to produce steam for sterilization of the nutrient medium, decreased requirements for pumping gaseous streams and decreased requirements for moving, handling and agitation of large batch mixtures. In addition, overall utilization of nutrient medium is improved in the process and apparatus of the present invention.

Upon completion of the reaction, yeast is withdrawn from the reaction zone 60 by means of line 62 and passed into collection tank 64, from which a portion is withdrawn as product via line 66 and a portion of which is passed via line 68 to pump 70 for reintroduction into the reaction zone via line 58. From the collection tank 64, product yeast is collected in a surge tank 72 into which air or other oxygen-containing gas is introduced via pump 74 and line 76 to maintain the yeast therein under constant aeration. From tank 72, yeast is withdrawn via line 78 and pump 80 to centrifuge 82. The centrifuge separates yeast cream and passes it via line 84 to storage tank 86. The liquor removed by the centrifuge 82 can be recycled to the process, discarded or otherwise used in separate processing.

In the foregoing illustrative embodiment, the molasses nutrient medium can be augmented with various additional nutrients, phosphates, nitrogenous materials, etc. While these materials can be incorporated within the molasses prior to feeding into the spirally-wound membrane, it generally is preferred to add these materials to the nutrient medium after it has been ultrafiltered through the spirally-wound membrane (e.g., either into annular chamber 36 or directly into reaction zone 60).

Figure 2:
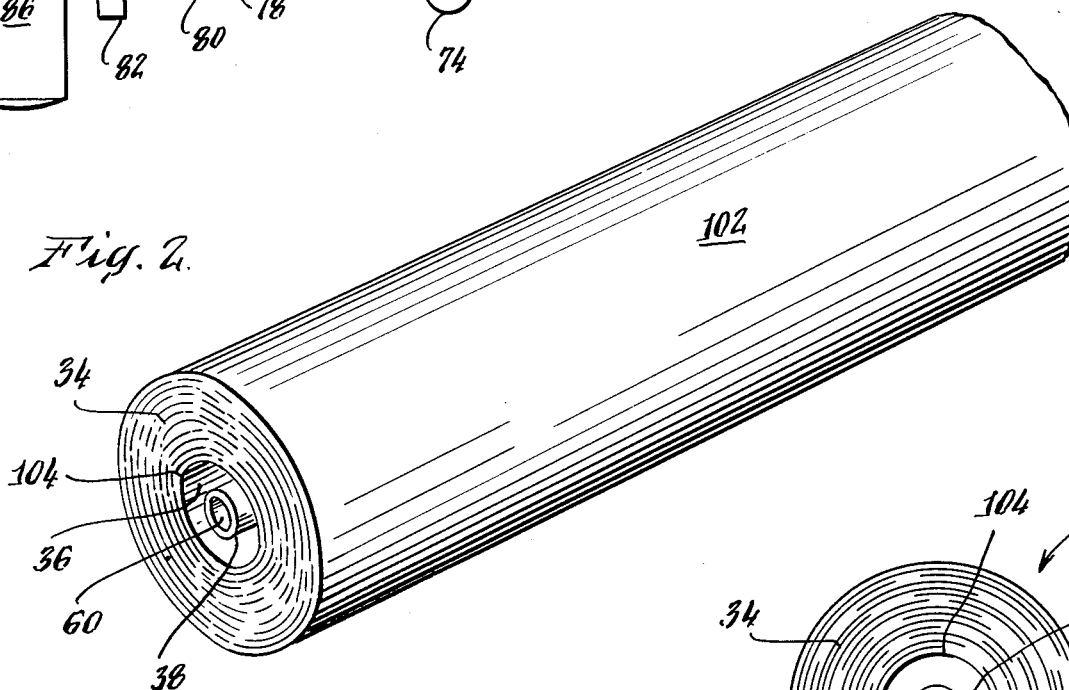
FIG. 2 is a perspective view of a spirally-wound ultrafiltration membrane according to the present invention, wherein a tubular membrane, within which microorganism propagation occurs, is arranged as an intimate part of the spirally-wound membrane.
Figure 3:
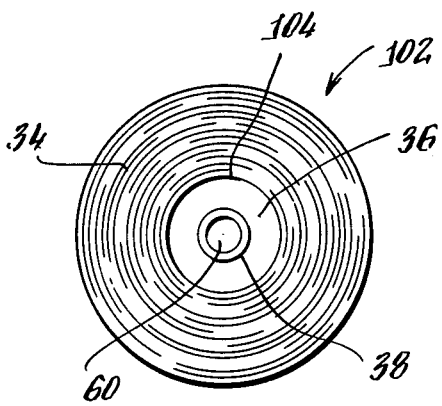
FIG. 3 is a cross-sectional view taken along plane 3—3 of FIG. 2.

In FIG. 2 there is shown, in perspective, a combination spirally-wound ultrafiltration unit and a tubular membrane, and FIG. 3 provides a cross-sectional view as an aid to this illustration.

The spirally-wound ultrafiltration membrane consists of a cylindrical outer shell 102 and a concentric inner surface 104. Between these surfaces, layers of essentially concentric, spirally-wound membrane material 34 are displaced. Inner surface 104 may itself be a membrane layer, but typically is a perforate support layer (particularly where the tubular membrane is arranged to be spaced-apart therefrom).

Inner layer 104 defines throughout the length of the spirally-wound membrane element an interior cylindrical space, into which is arranged a tubular membrane having an outer cylindrical membrane surface 38 and an inner hollow cylindrical space 60 which serves as the reaction zone. The outer surface 38 of the tubular membrane and the inner surface 104 of the spirally-wound membrane element define an annular chamber 36. The various elements are maintained in their fixed relative positions through use of suitable end-capping supports or housings (not shown) and/or through use of spacers provided along the length of the assembly.

Flow of nutrient medium into an end of the spirally-wound membrane (typically at points toward the outer periphery of the membrane layers) results in a substantially radial flow of a portion of the nutrient medium (permeate) from which the membrane excludes solids (impurities) above a particular size or molecular weight. The permeate moves into annular chamber 36 from which it then passes through outer membrane surface 38 of the tubular membrane into reaction zone 60. Gaseous material, nutrient medium supplements, etc. may be independently passed into annular chamber 36 (and/or into reaction zone 60 along with microorganisms).

The invention is further illustrated with reference to the following embodiment example.

EXAMPLE

According to this example, yeast is cultured in an apparatus of the type shown in the accompanying figures with the exception that the tubular filtration membrane 38 is not positioned concentrically within the spirally-wound membrane 34. According to this illustrative example, the tubular membrane will be positioned in a separate cartridge downstream of the unit 34. According to this example, cane or beet molasses or a mixture thereof, diluted to a brix of 25° to 40° by the addition of water, is passed through a spirally-wound ultrafiltration membrane of the ABCOR cartridge type and permeate is collected and passed to a tubular filtration membrane held in a cartridge of the Milipore type. Air is sparged into the permeate prior to passage through the tubular filtration membrane itself. A suspension of Bios 329 yeast having a solids content of about 1 to 10% is flowed through the interior of the tubular filtration membrane while the permeate containing highly dispersed air is flowed countercurrently to the yeast on the outside of the tubular membrane. Yeast is thereby produced continuously within a reaction zone which is comprised in the means for purifying the yeast culture medium.

The above description is for the purpose of teaching the person of ordinary skill in the art how to practice the present invention and is not intended to set forth in detail all of the obvious modifications and variations which will become apparent to the skilled worker upon reading. It is intended, however, to include all such modifications and variations within the scope of the present invention which is defined by the following claims.

What is claimed is:

1. A process for continuously propagating yeast in a purified nutrient medium comprising molasses, comprising the steps of:
   (a) continuously flowing a liquid nutrient medium comprising molasses under positive pressure through the length of a cylindrical, spirally-wound ultrafiltration membrane having a cylindrical outer surface and a cylindrical inner surface concentric therewith and which is separated from said outer surface by concentric layers of said spirally-wound ultrafiltration membrane, said inner surface defining an interior cylindrical space throughout the length of said cylindrical spirally-wound ultrafiltration membrane, whereby there is established a substantially radial flow of said nutrient medium into said interior cylindrical space, said radial flow of nutrient medium having removed therefrom solids having a molecular weight above about 30,000 daltons;
   (b) establishing a continuous flow of yeast through the hollow cylindrical interior of a tubular membrane material, said tubular membrane material being arranged within the interior cylindrical space of said spirally-wound ultrafiltration membrane so as to be substantially concentric therewith and such that the inner surface of the spirally-wound ultrafiltration membrane and the outer surface of said tubular membrane are spaced apart and define an annular chamber, whereby at least a portion of the nutrient medium obtained from said spirally-wound ultrafiltration membrane passes through the outer surface of said tubular membrane for contact with the yeast within the hollow cylindrical interior of said tubular membrane, said tubular membrane having an average pore diameter of from about 0.2 to 1.2 microns;
   (c) flowing an oxygen-containing gas either through said annular chamber for mixing with nutrient medium from said spirally-wound ultrafiltration membrane and/or through the hollow cylindrical interior of said tubular membrane;
   (d) maintaining conditions within said hollow cylindrical interior of said tubular membrane effective to propagate said yeast in said nutrient medium therein; and
   (e) continuously removing from said hollow cylindrical interior of said tubular membrane propagated yeast and nutrient medium.

2. The process according to claim 1 wherein said spirally-wound ultrafiltration membrane and said tubular membrane are effective to reduce the microorganism count of said nutrient medium passing into the hollow cylindrical interior of said tubular membrane to less than about 10 microorganisms per 100 grams of nutrient medium.

3. The process according to claim 2 wherein said oxygen-containing gas is flowed through said annular chamber and wherein the flow of said nutrient medium through the length of said spirally-wound ultrafiltration membrane and the flow of oxygen-containing gas into said annular chamber are countercurrent to the flow of yeast in the hollow cylindrical interior of said tubular membrane.

4. The process according to claim 1 wherein said oxygen-containing gas contains at least about 50% oxygen on a volume basis.

* * * * *